United States Patent [19]

Halter et al.

[11] Patent Number: 5,659,075

[45] Date of Patent: Aug. 19, 1997

[54] CHEMICAL PROCESS FOR PREPARING AN OPTICALLY ACTIVE AMINODIOL

[75] Inventors: Bernard Charles Halter, Stevenage, Great Britain; Clive Alwin Meerholz, Chapel Hill, N.C.; Mark Brian Schilling; David Joszef Tapolczay, both of Stevenage, Great Britain; John Peter Turnbull, Greenford, Great Britain

[73] Assignee: Glaxo Group Limited, Greenford, Great Britain

[21] Appl. No.: 387,834

[22] PCT Filed: Aug. 19, 1993

[86] PCT No.: PCT/EP93/02219

§ 371 Date: Apr. 6, 1995

§ 102(e) Date: Apr. 6, 1995

[87] PCT Pub. No.: WO94/04486

PCT Pub. Date: Mar. 3, 1994

[30] Foreign Application Priority Data

Aug. 21, 1992 [GB] United Kingdom ............... 9217823

[51] Int. Cl.$^6$ ................................................. C07C 51/16
[52] U.S. Cl. ...................... 562/455; 548/512; 564/184; 564/360; 564/414; 564/448
[58] Field of Search .............................. 564/448, 360, 564/184, 512, 455, 414

[56] References Cited

U.S. PATENT DOCUMENTS 3,474,093  10/1969  McCaully ............................ 260/247.1
3,972,944  8/1976  Beregi et al. ........................... 424/274

FOREIGN PATENT DOCUMENTS 0349242  3/1990  European Pat. Off. .

OTHER PUBLICATIONS

M. Mahmoudian, et al., "Resolution of 4-Aminocyclopentanecarboxylic Acid Methyl Esters Using Hydrolytic Enzymes," *Enzyme and Microbial Technology*, 14, No. 11, pp. 911–916, Nov. 1992.

J. Beres, et al., "Stereospecific Synthesis of (+)-Carbocyclic 2'-Deoxyadenosine. An Improved Procedure for the Preparation of (+)-(1R,2S,4R)-4-Amino-2-Hydroxy-1-Hydroxy Methylcyclopentane," *Tetrahedron*, 44, No. 19, pp.6207–6215, 1988.

L. ötvös, et al., "The First Stereospecific Synthesis of (+)-(1R,2S,4R)-4-Amino-2Hydro XY-1-Cyclopentanemethanol and (+)-Carbocyclic Thymidine," *Tetrahedron*, 28, No. 50, pp. 6381–6384, 1987.

Y. Fulmer Shealy, et al., "Carbocyclic Analogs of Thymidine Nucleosides and Related 1-Substituted thymines," *J. of Heterocyclic Chemistry*, 18, pp. 383–389, Aug. 1980.

Y. Fulmer Shealy, et al., "Carbocyclic Analogs of 2'Deoxyadenosine and 3'-Deoxyadenosine," *Tetrahedron Letters*, 27, pp. 2231–2234, 1969.

*Primary Examiner*—Brian M. Burn
*Attorney, Agent, or Firm*—Charles E. Dadswell

[57] ABSTRACT

A process is claimed for preparing [1S(1(α, 2β, 4β)]-4-amino-2-hydroxymethyl -1-cyclopentanol from cis-4-((R)-benzoylamino)-2-cyclopentenecarboxylic acid, methyl ester in five steps. The invention also describes a number of novel intermediates useful in the synthesis of [1S(1α, 2β,4β)]-4-amino-2-hydroxymethyl-1-cyclopentanol.

10 Claims, No Drawings

CHEMICAL PROCESS FOR PREPARING AN OPTICALLY ACTIVE AMINODIOL

This application is a 371 of PCT/EP93/02219, filed Aug. 19, 1993.

This invention relates to a new process to an optically active aminodiol which may be used to prepare chiral carbocyclic analogues of nucleosides.

During the past two decades much attention has been given to the synthesis and biological studies of carbocyclic analogues of nucleosides. Recently, a number of approaches have appeared in the literature for the preparation of enantiomerically pure carba-2'-deoxyribonucleotides, for example chemoenzymatically, by asymmetric synthesis and by chromatographic and enzymatic resolution. A key synthetic precursor of the carbocyclic analogues of 2'-deoxyribonucleotides is [1S(1α, 2β, 4β)]-4-amino-2-hydroxymethyl-1-cyclopentanol, a compound of formula (I) below first described by L Ötvös et al in Tetrahedron Letters, 28 (50), 6381–6384, 1987.

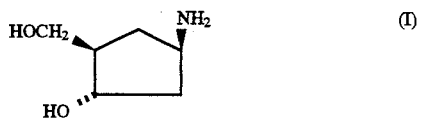

This paper described the preparation of the compound of formula (I) from an unsaturated bicyclic lactone, (+)-(1R,5S)-2-oxabicyclo[3.3.0]oct-6-en-3-one. The authors subsequently reported in Tetrahedron, 44(19), 6207–6216, 1988 an improved procedure from a bicyclic lactone diol.

We now describe herein a novel alternative procedure for the preparation of the compound of formula (I). Thus, according to one aspect of this invention, there is provided a multistep process for preparing the compound of formula (I) as depicted in Scheme 1 hereinafter.

in a solvent such as a halogenated hydrocarbon (e.g. dichloromethane) conveniently in admixture with a hydrocarbon solvent (e.g. toluene) at about room temperature, followed by reduction with a suitable hydride reducing agent, for example an aluminium hydride reducing agent such as diisobutylaluminium hydride (DIBAL). The DIBAL may conveniently be added as a solution in a hydrocarbon solvent (e.g. toluene) and the reduction carried out at a reduced temperature (e.g. at about 0° to 10° C.). The reaction may be completed by addition of a suitable inorganic acid such as hydrochloric acid.

Step c for the preparation of compounds of formula (III) from the compound of formula (IV) comprises treating (IV) with a suitable reagent to introduce the protecting group R. The group R may, for instance, represent an aralkyl group such as benzyl which can be introduced under conventional conditions. Thus, for example, benzylation may be effected by adding a benzyl halide (e.g. benzyl bromide) to (IV) in a solvent such as a hydrocarbon (e.g. toluene), preferably in the presence of a base such as an alkali or alkaline earth metal carbonate or bicarbonate (e.g. potassium carbonate).

Step d for the preparation of compounds of formula (II) from compounds of formula (III) comprises treating (III) with a hindered hydroborating agent capable of complexing to a tertiary amide such as disiamylborane in a solvent such as an ether (e.g. tetrahydrofuran) at about room temperature, followed by peroxide oxidation, for example using hydrogen peroxide. The oxidation step may be carried out in the presence of a strong inorganic base such as sodium hydroxide and at a reduced temperature (e.g. 0° to 15° C.). The work-up conditions may provide a compound of formula (II) in the form of a salt (e.g. a hydrochloride salt).

Step e for the preparation of the compound of formula (I) from compounds of formula (II) comprises a conventional deprotection step. Thus, for example, when R represents an aralkyl group such as benzyl, the deprotection step may conveniently be carried out by hydrogenolysis in the presence of a Noble metal catalyst such as palladium-on-carbon. The work-up conditions may provide the compound of formula (I) in the form of a salt (e.g. a hydrochloride salt).

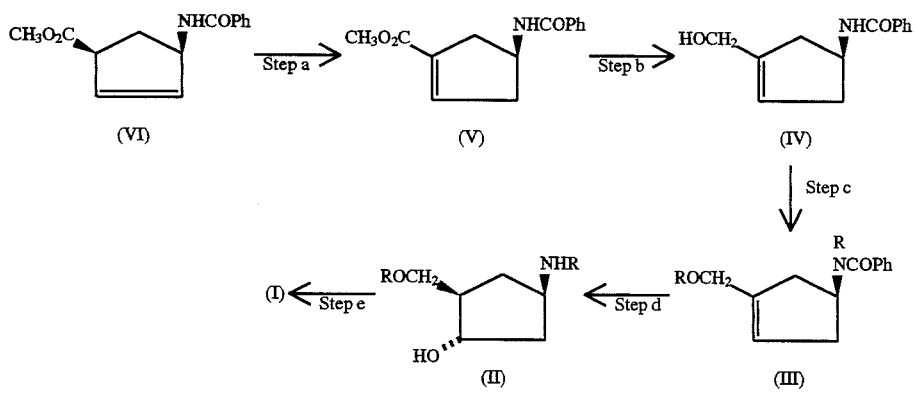

Scheme 1 wherein R represents a suitable protecting group.

Step a for the preparation of the compound of formula (V) from the compound of formula (VI) comprises treating (VI) with a suitable base such as an organic amine [e.g. 1,5-diazabicyclo[5.4.0]undec-5-ene (DBU)]. The reaction may conveniently be effected in an organic solvent such as a halogenated hydrocarbon (e.g. dichloromethane) at an elevated temperature (e.g. reflux).

Step b for the preparation of the compound of formula (IV) from the compound of formula (V) comprises treating (V) with a Lewis acid such as aluminium trichloride, zinc chloride, titanium tetrachloride or boron trifluoride etherate The combination of Steps a to e above provides an efficient and high yielding multistep synthesis of the compound of formula (I). In particular, the inclusion of a Lewis acid such as aluminium trichloride in process Step b provides an unexpected significant yield increase in product (IV), typically a 30 to 40% increase in yield. Furthermore, the use of a hindered hydroborating agent such as disiamylborane leads to a more regioselective and stereoselective hydroxylation reaction in Step d.

The preparation of the compound of formula (IV) from the compound of formula (V) (as defined by Step b hereinabove) is a key step in the Scheme 1 sequence and thus represents a particular or alternative aspect of the present invention.

The preparation of compounds of formula (II) from compounds of formula (III) (as defined by Step d hereinabove) is another key step in the Scheme 1 sequence and thus represents a further particular or alternative aspect of the present invention.

It is to be understood that, in addition to individual Steps b and d above, any sequential combinations of steps involving Step b and/or Step d in Scheme 1 represent further particular or alternative aspects of the present invention.

The compound of formula (VI) may be prepared by treating the compound of formula (VII)

(VII) [structure: cyclopentene with C=O and NCOPh]

with methanol in the presence of a strong acid such as sulphuric acid, conveniently with warming to about 35° to 50° C.

The compound of formula (VII) may be prepared from "(−)Vince Lactam", a compound of formula (VIII)

(VIII) [structure: cyclopentene with C=O and NH]

The acylation reaction may be carried out under conventional conditions, for example by treating (VIII) with a benzoyl halide (e.g. benzoyl chloride) in the presence of an organic amine base (e.g. pyridine) at about room temperature.

The compound of formula (VI) may also be prepared from "racemic Vince Lactam" (XII) according to Scheme 2 hereinafter.

Scheme 2

(XII) [structure with NH] —Step 1→ (XI) [structure with NCOPh] —Step 2→ (X) [HO₂C ... NHCOPh] —Step 3→ (IX) [HO₂C ... NHCOPh] —Step 4→ (VI)

Step 1 for the preparation of the compound of formula (XI) from the compound of formula (XII) comprises acylation following the method described above for preparing the compound of formula (VII) from the compound of formula (VIII).

Step 2 for the preparation of the compound of formula (X) from the compound of formula (XI) comprises treating (XI) with a suitable acid such as sulphuric acid or p-toluenesulphonic acid. The reaction may conveniently be carried out in an organic solvent such as acetonitrile or an ether (e.g. tetrahydrofuran) at an elevated temperature (e.g. reflux).

Step 3 for the preparation of the compound of formula (IX) from the compound of formula (X) comprises treating (X) with a suitable chiral resolving agent. Chiral resolving agents capable of effecting the desired conversion will be familiar to persons of ordinary skill in the art. One such suitable agent is R-(+)-α-methylbenzylamine which may be reacted with the compound of formula (X) in a solvent such as acetonitrile, optionally containing water, to provide the salt of formula (XIII)

(XIII) [structure: Ph—C(NH₃⁺)(Me)—H   ⁻O₂C...NHCOPh]

which may then be hydrolysed to the desired compound (IX) by addition of a suitable base such as sodium hydroxide.

Step 4 for the preparation of the compound of formula (VI) from the compound of formula (IX) comprises treating (IX) with methanolic hydrogen chloride at about room temperature.

The compounds of formulae (VIII) and (XII) are known compounds described in J. Chem. Soc. Perkin Trans. 1, 1992, (5), 589–592 and Tetrahedron Letters, 1976, (35), 3005–3008 respectively.

The compounds of formulae (II), (III), (IV), (V), (VI), (VII), (IX), (X), (XI) and (XIII) are novel intermediates and represent further aspects of the present invention. The compound of formula (VI) is a key novel intermediate and represents a particular aspect of the present invention.

The following non-limiting examples illustrate the invention.

Preparation 1 (step 1)
(±)-2-Benzoyl-2-azabicyclo [2.2.1]hept-5-ene-3-one (Intermediate XI)

Intermediate (XII) ("Racemic Vince Lactam") (32.3 g) was dissolved in pyridine (163 mL). The solution was cooled in ice while benzoyl chloride (50 mL) was added over approximately 10 minutes. The resulting dark red mixture was stirred at room temperature for 2 hours and then cooled to 15° C. Distilled water (490 mL) was added over 20 minutes and the developing slurry was stirred for 1 hour at room temperature then for 30 minutes at 10°–15° C. The solid was collected by vacuum filtration, washed thoroughly with water and dried at 50° C. under reduced pressure to afford the title compound (54 g).

δ (DMSO.d₆): 7.7–7.35 (5H,m); 7.07 (1H,m); 6.69 (1H, m); 5.08 (1H, m); 3.42 (1H,m); 2.49 (1H,m); 2.19 (1H,m). Mpt=110° C.

Preparation 2 (step 2)
cis-4-(Benzoylamino)-2-cyclopentene carboxylic acid (Intermediate X)

Intermediate (XI) (53 g) was dissolved in acetonitrile (410 mL) and decolourizing charcoal (12 g) was added. The mixture was stirred for 30 minutes at room temperature then filtered under vacuum through a bed of celite directly into a 1 liter round bottomed flask. Acetonitrile (140 mL) was used to wash the pad of celite. p-Toluenesulphonic acid monohydrate (4.75 g) and water (9.0 mL) were added and the stirred mixture was heated under gentle reflux for 1.5 hours. The stirred mixture was then cooled to room temperature over approximately 1 hour. Stirring was continued at this temperature for a further 1 hour before cooling to 10° C. for a further 1.5 hours. The deposited solid was collected by vacuum filtration, washed with acetonitrile (2×70 mL) and dried at 40° C. under vacuum to give the title compound (47.6 g).

δ (DMSO.d$_6$): 8.44 (1H, d, 6); 7.88 (2H, d, 8); 7.60–7.35 (3H,m); 6.00–5.80 (2H,m); 5.02 (1H,m); 3.52 (1H,m); 2.65–2.45 (1H,m); 2.05–1.80 (1 H,m).

Mpt=169° C.

Preparation 3 (step 3)
(R)-4-(Benzoylamino)-2-cyclopentene carboxylic acid (Intermediate IX)

Intermediate (X) (76 g) in acetonitrile (2.3 liters) and distilled water (105 mL) were stirred and warmed to 40°–45° C. A solution of (R)-(+)-α-methylbenzylamine (39.9 g) in acetonitrile (330 mL) was added at 45° C. to give a clear almost colourless solution. After 10 minutes crystallisation had begun. The continuously stirred mixture was cooled slowly over 90 minutes to room temperature, then chilled in ice water at 0°–5° C. for 2 hours. The deposited solid was collected by vacuum filtration, washed with chilled acetonitrile (3×140 mL) and dried at 40°–45° C. under reduced pressure overnight to give intermediate (XIII) (53.4 g). A suspension of intermediate (XIII) (52.9 g) in distilled water (530 mL) and methyl isobutyl ketone (530 mL) was stirred and the pH adjusted from approximately 6.7 to 9.5 by the slow addition of 2M aqueous sodium hydroxide solution. Stirring was continued for a further 30 minutes before the layers were allowed to separate. The aqueous layer was run off and re-extracted with methyl isobutyl ketone (150 mL). The separated aqueous layer was stirred and acidified to pH<2 by slow addition of 3M aqueous hydrochloric acid. The resulting slurry was stirred for 2 hours cooling to 10° C. and filtered. The solid was washed with distilled water and dried at 40°–50° C. under reduced pressure to give the title compound (33.2 g).

δ (DMSO.d$_6$): 8.49 (1H, d, 6); 8.00–7.80 (2H,m); 7.60–7.40 (3H,m); 6.00–5.80 (2H,m); 5.04 (1H,m); 3.54 (1 H,m); 2.65–2.45 (1 H,m); 2.05–1.85 (1H,m).

Mpt=146° C.

[α]$_D^{20}$+24° (c=0.5%, MeOH).

Preparation 4 (step 4)
cis-4-((R)-Benzoylamino)-2-cyclopentenecarboxylic acid, methyl ester (Intermediate VI)

Intermediate (IX) (37.8 g) in methanolic hydrogen chloride (260 mL, 4.5% w/w) was stirred at room temperature for 1.25 hours. The solution was concentrated under reduced pressure to a residual volume of 95 mL. To the resulting stirred solution was added distilled water (380 mL). The resulting suspension was stirred and cooled to between 5° and 10° C. for 2 hours. The solid was collected by vacuum filtration, washed with water (3×100 mL) and dried at 50° C. under reduced pressure to yield the title compound (37 g).

δ (DMSO.d$_6$): 8.56 (1H, d, 6); 8.05–7.85 (2H,m); 7.70–7.40 (3H,m); 6.10–5.85 (2H,m); 5.09 (1H,m); 3.71 (3H,s); 3.67 (1H,m); 2.80–2.50 (1H,m); 2.10–1.90 (1H,m).

Mpt=84° C.

[α]$_D^{20}$=+14 (c=0.5%, MeOH).

Preparation 5 (step a)
(S)-4-(Benzoylamino)-1-cyclopentene carboxylic acid methyl ester (Intermediate V)

Intermediate (VI) (20 g) was dissolved in dichloromethane (100 mL) and 1,5-diazabicyclo [5.4.0] undec-5-ene (17.4 mL) was added. The reaction was stirred at reflux for 6 hours before cooling to room temperature. Stirring was continued at room temperature overnight. The batch was cooled to 0° C. and ice (30 g ), water (20 mL) and concentrated sulphuric acid (6.0 mL) were added. The organic phase was separated and washed with water (50 mL). Concentration of the separated organic phase under reduced pressure yielded a soft solid which was triturated with diisopropyl ether (50 mL). The product was collected by filtration, washed with diisopropyl ether and dried under vacuum to give the title compound (18.76 g).

δ (DMSO.d$_6$) 8.59 (1H,d,$_6$); 7.89 (2H,m); 7.60–7.35 (3H,m); 6.78 (1H,m); 4.62 (1H,m); 3.73 (3H,s); 3.05–2.80 (2H,m); 2.70–2.40 (2H,m).

Preparation 6 (step b)
(S)-N-[3-(Hydroxymethyl)-3-cyclopentenyl]-benzamide (Intermediate IV)

Intermediate (V) (40 g) was suspended in a mixture of dichloromethane (200 mL) and toluene (100 mL) and the suspension was cooled to approximately 3° C. Aluminium trichloride (21.75 g) was added and the reaction mixture was stirred for 20 minutes to give a cloudy solution. The resultant mixture was then cooled to 0° C. and a solution of diisobutylaluminium hydride in toluene (100 mL, 375 mmol of diisobutylaluminium hydride) was added at a rate such that the reaction mixture remained in the temperature range of 0°–10° C. Upon completion of the addition of the diisobutylaluminium hydride the reaction mixture was stirred for 10 minutes at 0°–5° C. After this time the mixture was added over 16 minutes to a solution of concentrated hydrochloric acid (100 mL) in water (200 mL) at room temperature. Toluene (100 mL) was added and stirring continued for a further 30 minutes. The reaction mixture was then cooled to 5° C. and stirred at this temperature for 1 hour. The product was harvested by filtration and washed with toluene (2×80 mL), 2M hydrochloric acid (40 mL) and water (40 mL). Drying under vacuum yielded the title compound (32.36 g).

δ (DMSO.d$_6$): 8.49 (1H,d,6); 7.87 (2H,m); 7.60–7.40 (3H,m); 5.51 (1H,m); 4.70 (1H,m), 4.60 (1H,m); 4.60 (1H, m); 3.99 (2H,s,broad); 2.80–2.55 (2H,m); 2.45–2.20 (2H, m).

n (max, nujol): 3389 cm$^{-1}$, 3315 cm$^{-1}$, 1629 cm$^{-1}$.

Preparation 7 (step c)
(S)-N-(Phenylmethyl)-N-[3[(phenylmethoxy)methyl]-3-cyclopentenyl]-benzamide (Intermediate III)

Intermediate (IV) (500 g) was added to t-butyl methyl ether (5 L) and the resultant suspension stirred at room temperature while potassium carbonate (1906 g), tetra-n-butylammonium hydrogen sulphate (117 g) and sodium hydroxide (644 g) were added sequentially. Stirring was continued while the internal temperature was raised to reflux via a hot water bath. Reflux was continued for a further 25 minutes and then benzyl bromide (600 ml) was added dropwise to the refluxing suspension. Reflux was continued for a further 160 min. with further benzyl bromide (25 ml) added after 2 h. Heating was discontinued and methanol (25 ml) added over 30 seconds. The mixture was then cooled to 30.8° C. and distilled water (5×1 L) added over 4 minutes. The mixture was further cooled with a cold water bath, transferred to a glass separating flask via vacuum and the lower aqueous phase removed. The aqueous phase was extracted with t-butyl methyl ether (1 L) and the organic phases combined and washed with distilled water (3×2.5 L). The organic phase was concentrated to 1.25 L and stirred for 20 minutes. Petroleum ether (60°–80°, 2 L) was then added dropwise and stirring continued for a further 20 minutes. After refrigeration overnight, the resulting solid was filtered off and washed with chilled petroleum ether (60°–80°, 2×1 L) under vacuum. The solid was then dried to give the title compound (737.6 g).

δ (DMSO.D$_6$): 7.1–7.6 (15H, m), 5.52 (1H, broad s), 4.6 (3H, m), 4.38 (2H, s), 3.90 (2H, s), 2.40 (4H, broad m).

Mpt=74°–75° C.

Preparation 8 (step d)

[1S(1α,2β,4β)]-4-[(Phenylmethyl)amino]-2-[(phenylmethoxy)methyl]-1-cyclopentanol (Intermediate II)

2-methyl-2-butene (202 ml) was added to tetrahydrofuran (198 ml) and the resulting solution stirred under nitrogen and cooled to 0° C. Borane dimethylsulphide complex (90.6 ml) was then added at a rate such that the temperature of the mixture did not exceed 24° C. This solution was then stirred and treated with a solution of Intermediate (III)(120 g) in tetrahydrofuran (240 ml) over 40 minutes. Stirring was continued for 24 h at ca 23°–26° C. and then the reaction quenched by cooling the solution to 0° C. and adding dropwise a mixture of water (10.9 ml) and tetrahydrofuran (120 ml). The solution was re-cooled to 0° C. and then 3M sodium hydroxide (302 ml) added over 12 minutes. The solution/emulsion obtained was cooled to −20° to −25° C. and hydrogen peroxide (30%, 308 ml) added dropwise over ca 2 hours such that an internal temperature of <30° C. was maintained. 98 minutes from the end of the hydrogen peroxide addition a solution of sodium sulphite (60 g) in water (240 ml) was added over 70 minutes. Following the final addition of hydrogen peroxide the mixture was left under nitrogen overnight. The mixture was then stirred and methyl isobutyl ketone (600 ml) was added. The phases were separated and the aqueous phase was extracted with methyl isobutyl ketone (240 ml). The combined organic phases were washed with water (4×240 ml) and the organic phase reduced to ca 600 ml volume. The resulting yellow solution was stirred and cooled to 4° C. and then concentrated hydrochloric acid (25 ml) was added. The cooling bath was removed and after 30 minutes t-butyl methyl ether (600 ml) was added dropwise. The pH was lowered to 1–2 during the addition of t-butyl methyl ether by further addition of concentrated hydrochloric acid (0.5 ml). The resulting suspension was stirred for ca 1 h with ice/water cooling and then filtered. The residual white solid was washed with t-butyl methyl ether (3×240 ml) and then dried to give the title compound (89.7 g).

δ (DMSO.d$_6$): 9.6 (2H, broad), 7.7–7.2 (10H, m), 4.90 (1H, broad), 4.48 (2H, AB), 4.10 (2H, m), 3.98 (1H, m), 3.5 and 3.35 (3H, m), 2.25, 1.8–2.1, 1.52 (5H, m).

Mpt=136°–138° C.

Preparation 9 (step e)

[1S(1α,2β,4β)]-4-Amino-2-hydroxymethyl-1-cyclopentanol

Intermediate (II) (100 g) was dissolved in isopropanol (250 mL) and water (80 mL). Charcoal (50 g) was added and the mixture stirred for 30 minutes. After this time celite (25 g) was added and the mixture filtered through a bed of celite. The filter bed was washed with a mixture of isopropanol (125 mL) and water (40 mL) twice. The filtrate and washes were combined. 5% Palladium on charcoal (100 g) was charged into a dry flask. The flask was purged with nitrogen and the combined filtrate and washes from above were added. The resulting mixture was stirred and heated to approximately 50° C. under an atmosphere of hydrogen for 3 hours. After this time the reaction mixture was allowed to cool and then filtered through a pad of celite. The filter pad was then washed with mixtures of isopropanol and water. The combined filtrate and washings were evaporated to approximately 400 mL. n-Butanol (200 mL) was added and the mixture re-evaporated under reduced pressure to 50 mL. Methanol (40 mL) containing concentrated hydrochloric acid (2 mL) was added followed by n-butanol (200 mL). The solvent was removed under reduced pressure to yield a gum. This was taken up in methanol and the volume reduced under pressure to the point at which crystallisation had just begun. The mixture was seeded with an authentic sample of the title compound and acetone (200 mL) was added slowly. Filtration followed by washing with n-butanol/acetone (1:1, 100 mL) and acetone (100 mL) yielded after drying, under reduced pressure, the title compound (39.3 g).

δ (DMSO:d$_6$): 8.20 (3H,s,broad); 4.90–4.50 (2H,m, broad); 3.94 (1H,m); 3.53 (1H,m); 3.50–3.25 (2H,m); 2.13 (1H,m); 1.95–1.70 (3H,m); 1.34 (1H,m).

Analysis Found: C=43.5, H=8.8, N=8.3,

Requires: C=43.0, H=8.4, N=8.4.

Preparation 10

(−)2-Benzoyl-2-azabicyclo[2.2.1]hept-5-ene-3-one (Intermediate VII)

A solution of Intermediate (VIII) ("(−)Vince Lactam") (1.4 kg) in pyridine (50 L) under nitrogen at ca 10° C. was treated with benzoyl chloride (15 L), keeping the temperature below 25° C. The mixture was stirred at 20° to 30° C. for 2.5 h, cooled to ca 10° C. and treated with water (30 L) over ca 30 minutes. Further water (120 L) was added and the mixture stirred at 5° C. overnight. The resulting solid was filtered, washed with water (4×20 L) and dried to give the title compound (16.9 Kg).

δ (DMSO.d$_6$): 7.7–7.4 (5H, m), 7.05 (1H, m), 6.70 (1H, m), 5.07 (1H, m), 3.42 (1H, broad s), 2.50 (1H, d), 2.18 (1H, d).

Mpt=153° C.

Preparation 11 cis-4-((R)-Benzoylamino)-2-cyctopentenecarboxylic acid, methyl ester (Intermediate VI)

Concentrated sulphuric acid (2.64 L) was added over 10 minutes to a stirred suspension of Intermediate (VII) (13.27 Kg) in methanol (60 L). A further 8 L methanol was added to the suspension which was slowly warmed to 47° C. The resulting solution was cooled to 25° C. and triethylamine (8.6 L) added over ca 10 minutes followed by water (90 L). Further triethylamine (3×200 ml) was added to give a final pH of ca 7–7.5. The methanol was distilled off in vacuo during which time further water (40 L) was added portionwise. The resulting slurry was cooled to 0° C. and stirred at this temperature overnight. The resulting solid was filtered, washed with water (3×25 L) and dried to give the title compound (14.42 Kg).

δ (DMSO.d$_6$): 8.55 (1H, d), 7.84 (2H, m), 7.6–7.4 (3H, m), 5.90 (2H, m), 5.02 (1H, m), 3.60 (1H, m) 2.58 (1H, dt), 1.92 (1H, dt).

Mpt=86° C.

We claim:

1. A process for the preparation of a compound of formula (I)

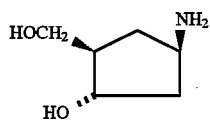

or a salt thereof from a compound of formula (VI)

which comprises:

Step a: treating a compound of formula (VI) with a suitable base to provide a compound of formula (V)

Step b: treating the so-formed compound of formula (V) with a Lewis acid, followed by reduction with a suitable hydride reducing agent to provide a compound of formula (IV)

Step c: protecting the so-formed compound of formula (IV) to provide a compound of formula (III)

where R is a protecting group

Step d: treating the so-formed compound of formula (III) with a hindered hydroborating agent capable of complexing a tertiary amide, followed by peroxide oxidation to provide a compound of formula (II)

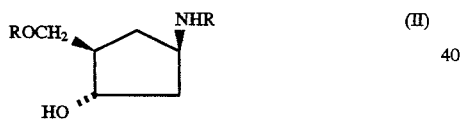

where R is a protecting group and

Step e: deprotecting the so-formed compound of formula (II) to provide the desired compound of formula (I).

2. A process for preparing a compound of formula (IV)

comprising treating a compound of formula (V)

with a Lewis acid, followed by reduction with a suitable hydride reducing agent.

3. A process as claimed in claim 2 in which the Lewis acid is aluminium trichloride.

4. A process as claimed in claim 2, which comprises treating a compound of formula (V) with aluminum trichloride in a solvent, followed by reduction with an aluminum hydride reducing agent.

5. A process for preparing a compound of formula (II)

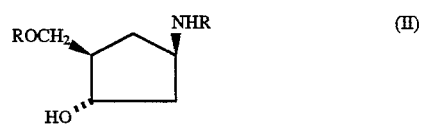

where R is a protecting group comprising treating a compound of formula (III)

where R is a protecting group with a hindered hydroborating agent capable of complexing to a tertiary amide, followed by peroxide oxidation.

6. A process as claimed in claim 5 in which the hydroborating agent is disiamylborane.

7. A process as claimed in claim 5 which comprises treating a compound of formula (III) with disiamylborane in a solvent followed by peroxide oxidation.

8. A process for preparing a compound of formula (IX)

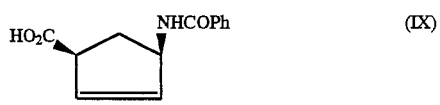

which comprises treating a compound of formula (X)

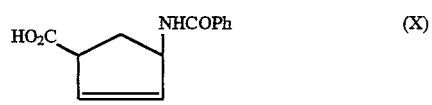

with R-(+)-α-methylbenzylamine to provide a compound of formula (XIII)

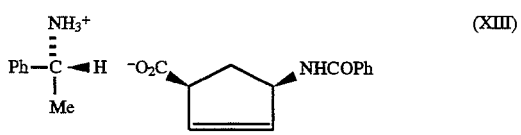

and then hydrolysing the so-formed compound of formula (XIII) under basic condition to provide the desired compound of formula (IX).

9. cis-4-((R)-Benzoylamino)-2-cyclopentenecarboxylic acid, methyl ester.

10. The compounds of the following formulae:

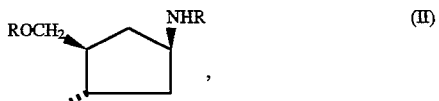

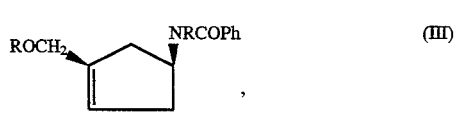

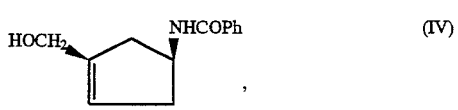

-continued
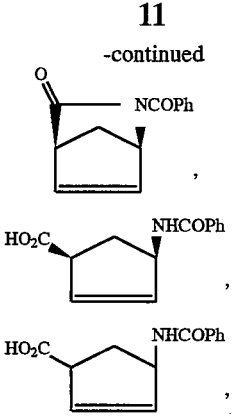
(VII)
(IX)
(X)
-continued
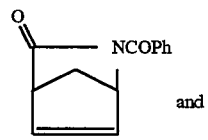
(XI)
and
(XIII)
* * * * *

UNITED STATES PATENT AND TRADEMARK OFFICE
CERTIFICATE OF CORRECTION

PATENT NO. : 5,659,075

DATED : August 19, 1997

INVENTOR(S) : Bernard Charles Halter, Clive Alwin Meerholz, Mark Brian Schilling, David Joszef Tapolczay and John Turnbull It is certified that error appears in the above-identified patent and that said Letters Patent is hereby corrected as shown below:

In claim 10, last line, after "(XIII)" insert ---wherein R is a protecting group---

In claim 10, after (XI) delete compound drawing XIII and substitute therefor:

--- 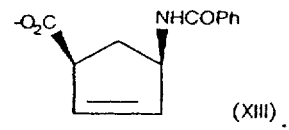 ---

Signed and Sealed this

Ninth Day of December, 1997

Attest:

BRUCE LEHMAN

Attesting Officer

Commissioner of Patents and Trademarks